United States Patent
Suzuki

(10) Patent No.: US 12,042,319 B2
(45) Date of Patent: Jul. 23, 2024

(54) MEDICAL IMAGE PROCESSING APPARATUS, X-RAY CT APPARATUS, METHOD OF MEDICAL IMAGE PROCESSING, AND COMPUTER PROGRAM PRODUCT

(71) Applicant: CANON MEDICAL SYSTEMS CORPORATION, Otawara (JP)

(72) Inventor: Yojiro Suzuki, Oyama (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 332 days.

(21) Appl. No.: 17/653,162

(22) Filed: Mar. 2, 2022

(65) Prior Publication Data
US 2022/0287667 A1    Sep. 15, 2022

(30) Foreign Application Priority Data

Mar. 11, 2021 (JP) ................. 2021-038914

(51) Int. Cl.
| | | |
|---|---|---|
| *G06T 7/80* | (2017.01) | |
| *A61B 6/00* | (2006.01) | |
| *A61B 6/03* | (2006.01) | |
| *A61B 6/46* | (2024.01) | |
| *G06N 20/00* | (2019.01) | |

(52) U.S. Cl.
CPC ............ *A61B 6/5205* (2013.01); *A61B 6/032* (2013.01); *A61B 6/54* (2013.01); *A61B 6/461* (2013.01); *G06N 20/00* (2019.01)

(58) Field of Classification Search
CPC ....... A61B 1/00; A61B 8/5215; A61B 8/5223; G06T 7/70; G06T 7/73; G06T 2207/20; G06T 2207/20004; G06T 2207/20021; G06T 2207/20084; G06T 2207/20104; G06T 2207/10116; G06T 2207/22081; G06T 7/174; G06T 2207/10081; G06T 7/97; G06N 3/08; G06N 5/00; G06N 20/00

See application file for complete search history.

(56) References Cited

U.S. PATENT DOCUMENTS

| | | | |
|---|---|---|---|
| 2019/0005354 A1 | 1/2019 | Nakamura | |
| 2020/0090371 A1* | 3/2020 | Hu | .......... H04N 23/60 |

FOREIGN PATENT DOCUMENTS

JP        2019-10411 A        1/2019

\* cited by examiner

*Primary Examiner* — Don K Wong
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry is configured to acquire first medical image data. The processing circuitry is configured to identify a region of interest in the first medical image data based on a learned model and the first medical image data. The learned model is trained based on second medical image data corresponding to the first medical image data and third medical image data different from the first medical image data in type and related to the same subject as a subject of the second medical image data. At least part of the third medical image data is higher in imaging sensitivity for a region of the subject corresponding to the region of interest than the second medical image data.

12 Claims, 7 Drawing Sheets

MEDICAL IMAGE PROCESSING APPARATUS, X-RAY CT APPARATUS, METHOD OF MEDICAL IMAGE PROCESSING, AND COMPUTER PROGRAM PRODUCT

CROSS-REFERENCE TO RELATED APPLICATIONS

This application is based upon and claims the benefit of priority from Japanese Patent Application No. 2021-038914, filed on Mar. 11, 2021; the entire contents of which are incorporated herein by reference.

FIELD

Embodiments disclosed herein relate generally to a medical image processing apparatus, an X-ray CT apparatus, a method of medical image processing, and a computer program product.

BACKGROUND

Conventionally, in medical image diagnosis using an X-ray computed tomography (CT) apparatus, an early CT sign (an early ischemia sign) has been used in some cases in order to detect hyperacute cerebral infarction, for example, for the purpose of detection in an early stage and performing appropriate treatment. In general, the X-ray CT apparatus enables quicker image reconstruction than a magnetic resonance imaging (MRI) apparatus from the viewpoint of workflow, thus involving a shorter time required for medical image diagnosis.

However, there is a problem in that high interpretation ability is required to detect the early CT sign, and thus medical image diagnosis using the early CT sign produces many false negatives. In addition, there is a problem in that medical image diagnosis based on a diffusion-weighted image (DWI) obtained with the MRI apparatus involves a longer time required for medical image diagnosis, although it has much higher ability to detect hyperacute cerebral infarction than that using the X-ray CT apparatus.

DETAILED DESCRIPTION

Figure 1:
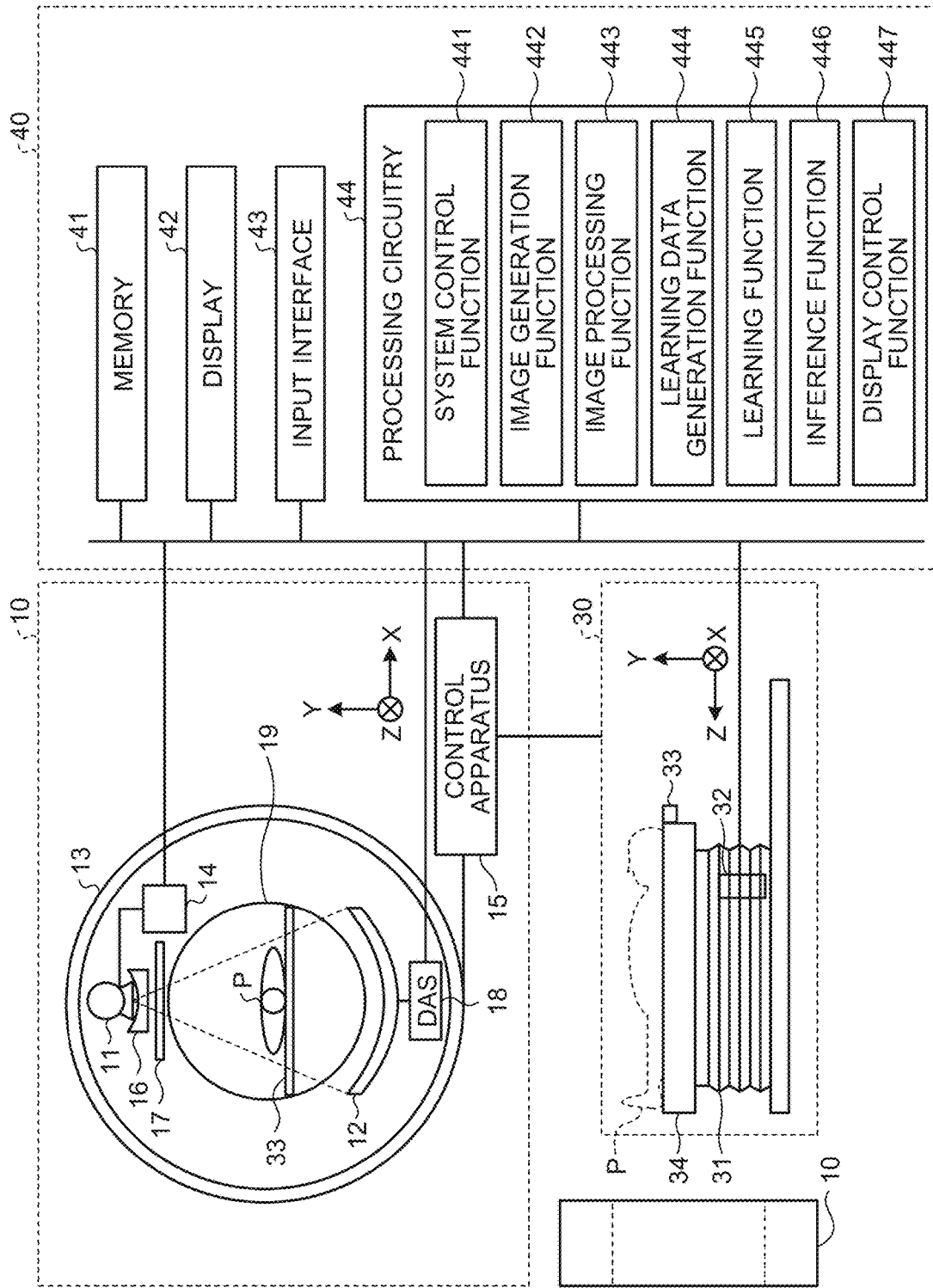
FIG. 1 is a diagram of an example of the configuration of an X-ray computed tomography (CT) apparatus in which a medical image processing apparatus according to an embodiment is installed.

A medical image processing apparatus according to an embodiment includes processing circuitry. The processing circuitry is configured to acquire first medical image data. The processing circuitry is configured to identify a region of interest in the first medical image data based on a learned model and the first medical image data. The learned model is trained based on second medical image data corresponding to the first medical image data and third medical image data different from the first medical image data in type and related to the same subject as a subject of the second medical image data. At least part of the third medical image data is higher in imaging sensitivity for a region of the subject corresponding to the region of interest than the second medical image data.

The following describes a medical image processing apparatus, an X-ray computed tomography (CT) apparatus, a method of medical image processing, and a computer program product according to embodiments with reference to the accompanying drawings. In the following description, components having the same or substantially the same function as those described above with respect to the previously described drawings will be denoted by the same symbols, and a duplicate description will be given only when necessary. Even when the same part is represented, the dimensions or proportions thereof may be represented in different ways depending on the drawings. From the viewpoint of ensuring the visibility of the drawings, for example, only major or representative components in the description of each of the drawings may be denoted by reference symbols, and even components having the same or substantially the same function are not necessarily denoted by reference symbols.

The embodiments described below exemplify cases in which the medical image processing apparatus according to each of the embodiments is installed in the X-ray CT apparatus.

The medical image processing apparatus according to the embodiments is not limited to the case in which it is installed in the X-ray CT apparatus and may be implemented as an independent apparatus by a computer having a processor such as a central processing unit (CPU) and memories such as a read only memory (ROM) and a random access memory (RAM) as hardware resources. In this case, the processor installed in the computer can implement various kinds of functions according to the embodiments by executing a computer program read from the ROM or the like and loaded onto the RAM.

The medical image processing apparatus according to the embodiments may be implemented by being installed in another medical image diagnostic apparatus than the X-ray CT apparatus. In this case, the processor installed in each medical image diagnostic apparatus can implement the functions according to the embodiments by executing a computer program read from the ROM or the like and loaded onto the RAM. Various kinds of functions according to the embodiments can be implemented. Examples of the other medical image diagnostic apparatus include various medical image diagnostic apparatuses such as X-ray diagnostic apparatuses, magnetic resonance imaging (MRI) apparatuses, ultrasonic diagnostic apparatuses, single photon emission computed tomography (SPECT) apparatuses, positron emission computed tomography (PET) apparatuses, SPECT-CT apparatuses, in which a SPECT apparatus and an X-ray CT apparatus are integrated with each other, and PET-CT apparatuses, in which a PET apparatus and an X-ray CT apparatus are integrated with each other.

X-ray CT apparatuses include various types such as the third-generation CT and the fourth-generation CT, for example; any of these types can be used for the embodiments. The third-generation CT is of the rotate/rotate type, in which an X-ray tube and a detector integrally rotate around a subject. The fourth-generation CT is the stationary/rotate type, in which many X-ray detection elements arranged in a ring shape are fixed, with only the X-ray tube rotating around the subject.

First Embodiment

FIG. 1 is a diagram of an example of the configuration of an X-ray CT apparatus 1 in which a medical image processing apparatus according to an embodiment is installed. The X-ray CT apparatus 1 applies X-rays from an X-ray tube 11 to a subject P and detects the applied X-rays with an X-ray detector 12. The X-ray CT apparatus 1 generates a CT image about the subject P based on output from the X-ray detector 12.

As illustrated in FIG. 1, the X-ray CT apparatus 1 has a frame 10, a couch 30, and a console 40. For the convenience of description, FIG. 1 depicts a plurality of frames 10. The frame 10 is a scanning apparatus having a configuration to take an X-ray CT image of the subject P. The couch 30 is a conveyance apparatus for placing the subject P to be subjected to X-ray CT imaging and positioning the subject P. The console 40 is a computer controlling the frame 10. The frame 10 and the couch 30 are installed in a CT examination room, whereas the console 40 is installed in a control room adjacent to the CT examination room, for example. The frame 10, the couch 30, and the console 40 are mutually communicably connected to each other in a wired or wireless manner.

The console 40 is not necessarily required to be installed in the control room. The console 40 may be installed in the same room together with the frame 10 and the couch 30, for example. The console 40 may be incorporated into the frame 10.

In the present embodiment, a rotating shaft of a rotating frame 13 in a non-tilted state or the longitudinal direction of a couchtop 33 of a couch 30 is defined as a Z-axial direction, an axial direction orthogonal to the Z-axial direction and horizontal to a floor surface is defined as an X-axial direction, and an axial direction orthogonal to the Z-axial direction and perpendicular to the floor surface is defined as a Y-axial direction.

As illustrated in FIG. 1, the frame 10 has the X-ray tube 11, the X-ray detector 12, the rotating frame 13, an X-ray high voltage apparatus 14, a control apparatus 15, a wedge 16, a collimator 17, and a data acquisition system (DAS) 18.

The X-ray tube 11 is a vacuum tube having a cathode (filament) generating thermoelectrons and an anode (target) generating X-rays upon collision with the thermoelectrons. The X-ray tube 11 applies the thermoelectrons from the cathode toward the anode using high voltage supplied from the X-ray high voltage apparatus 14 to apply X-rays to the subject P.

The hardware generating X-rays is not limited to the X-ray tube 11. In place of the X-ray tube 11, a fifth-generation system may be used to generate X-rays, for example. The fifth-generation system includes a focus coil focusing an electron beam generated from an electron gun, a deflection coil electromagnetically deflecting the electron beam, and a target ring surrounding half the subject P to generate X-rays upon collision with the deflected electron beam.

The X-ray detector 12 detects the X-rays emitted from the X-ray tube 11 and having passed through the subject P and outputs an electric signal corresponding to a detected X-ray dose to the DAS 18. The X-ray detector 12 has a row of X-ray detection elements in which a plurality of X-ray detection elements are arranged in a channel direction along one arc centered on the focal point of the X-ray tube 11, for example. The X-ray detector 12 has a structure in which a plurality of X-ray detection elements are arranged in a slice direction (a row direction) in the channel direction, for example. The X-ray detector 12 is an indirect conversion type detector having a grid, a scintillator array, and an optical sensor array, for example. The scintillator array has a plurality of scintillators. The scintillator has a scintillator crystal outputting light with a light amount corresponding to an incident X-ray dose. The grid is placed on a face of the scintillator array on its X-ray incident plane side and has an X-ray blocking plate having the function of absorbing scattered X-rays. The grid may also be referred to as a collimator (a one-dimensional collimator or a two-dimensional collimator). The optical sensor array has the function of converting the light from the scintillators into an electric signal corresponding to the light amount of the light. A photomultiplier tube (PMT) is used as the optical sensor, for example. The X-ray detector 12 may be a direct conversion type detector having a semiconductor element converting incident X-rays into an electric signal. The X-ray detector 12 is an example of a detector.

The rotating frame 13 is an annular frame supporting the X-ray tube 11 and the X-ray detector 12 such that they face each other and rotates the X-ray tube 11 and the X-ray detector 12 by the control apparatus 15 described below. An image field of view (FOV) is set in an aperture 19 of the rotating frame 13. The rotating frame 13 is a casting made of aluminum, for example. In addition to the X-ray tube 11 and the X-ray detector 12, the rotating frame 13 can further support the X-ray high voltage apparatus 14, the wedge 16, the collimator 17, and the DAS 18. The rotating frame 13 can also further support various components not illustrated in FIG. 1.

The X-ray high voltage apparatus 14 has a high voltage generation apparatus and an X-ray control apparatus. The high voltage generation apparatus has an electric circuit such as a transformer and a rectifier and generates high voltage to be applied to the X-ray tube 11 and a filament current to be supplied to the X-ray tube 11. The X-ray control apparatus controls output voltage according to the X-rays emitted by the X-ray tube 11. The high voltage generation apparatus may be of the transformer system or of the inverter system. The X-ray high voltage apparatus 14 may be provided in the rotating frame 13 in the frame 10 or be provided in a fixed frame (not illustrated) in the frame 10. The fixed frame is a frame rotatably supporting the rotating frame 13.

The control apparatus 15 includes drive mechanisms such as motors and actuators and processing circuitry having a processor and a memory to control the drive mechanisms. The control apparatus 15 receives input signals from an input interface 43, an input interface provided in the frame 10, or the like to perform operation control of the frame 10 and the couch 30. Examples of the operation control by the control apparatus 15 include control to rotate the rotating frame 13, control to tilt the frame 10, and control to operate the couch 30. The control to tilt the frame 10 is implemented by the control apparatus 15 rotating the rotating frame 13 about an axis parallel to the X-axial direction according to inclination angle (tilt angle) information input through the input interface mounted on the frame 10. The control apparatus 15 may be provided in the frame 10 or be provided in the console 40.

The wedge 16 is a filter for regulating an X-ray dose emitted from the X-ray tube 11. Specifically, the wedge 16 is a filter passing and attenuating the X-rays applied from the X-ray tube 11 so that the X-rays applied from the X-ray tube 11 to the subject P have distribution set in advance. The wedge 16 is a wedge filter or a bow-tie filter and is formed by machining aluminum or the like so as to have a certain target angle and a certain thickness, for example.

The collimator 17 limits the application range of the X-rays having passed through the wedge 16. The collimator 17 supports a plurality of lead plates blocking X-rays in a slidable manner and adjusts the form of a slit formed by the lead plates. The collimator 17 may also be called an X-ray aperture.

The DAS 18 reads the electric signal corresponding to the X-ray dose detected by the X-ray detector 12 from the X-ray detector 12. The DAS 18 amplifies the read electric signal and integrates (adds) the electric signal over a view period to collect detection data having digital values corresponding to an X-ray dose over the view period. The detection data is called projection data. The DAS 18 is implemented by an application specific integrated circuit (ASIC) in which a circuit element that can generate the projection data is installed, for example. The projection data is transmitted to the console 40 via a non-contact data transmission apparatus or the like. The DAS 18 is an example of the detector.

The detection data generated by the DAS 18 is transmitted to a receiver having a photodiode provided in a non-rotating part of the frame 10 (e.g., the fixed frame, which is not illustrated in FIG. 1) through optical communication from a transmitter having a light emitting diode (LED) provided in the rotating frame 13 and is transferred to the console 40. The method for transmitting the detection data from the rotating frame 13, which is a rotating part, to the non-rotating part of the frame 10 is not limited to the optical communication described above; any method may be adopted so long as it is non-contact data transfer.

The present embodiment describes the X-ray CT apparatus 1 in which the X-ray detector 12 of an integral type is installed as an example; the technology according to the present embodiment can also be implemented as the X-ray CT apparatus 1 in which a photon counting type X-ray detector is installed.

The couch 30 is an apparatus placing and moving the subject P to be scanned. The couch 30 has a base 31, a couch drive apparatus 32, the couchtop 33, and a support frame 34. The base 31 is a casing supporting the support frame 34 in a vertically movable manner. The couch drive apparatus 32 is a drive mechanism moving the couchtop 33 on which the subject P is placed in the longitudinal direction of the couchtop 33. The couch drive apparatus 32 includes motors and actuators. The couchtop 33 is a board on which the subject P is placed. The couchtop 33 is provided on a top face of the support frame 34. The couchtop 33 can protrude from the couch 30 toward the frame 10 so that the whole body of the subject P can be imaged. The couchtop 33 is formed of carbon fiber reinforced plastic (CFRP), for example, which has good X-ray permeability and physical properties such as rigidity and strength. The inside of the couchtop 33 is hollow, for example. The support frame 34 supports the couchtop 33 in a movable manner in the longitudinal direction of the couchtop 33. In addition to the couchtop 33, the couch drive apparatus 32 may move the support frame 34 in the longitudinal direction of the couchtop 33.

The console 40 has a memory 41, a display 42, the input interface 43 and processing circuitry 44. Data communication among the memory 41, the display 42, the input interface 43, and the processing circuitry 44 is performed via a bus. Although the console 40 is described as a separate unit from the frame 10, the frame 10 may include the console 40 or part of the components of the console 40.

The memory 41 is implemented by a semiconductor memory element such as a ROM, a RAM, or a flash memory, a hard disk, or an optical disc, for example. The memory 41 stores therein the projection data and reconstructed image data, for example. The memory 41 stores therein various kinds of computer programs, for example. The memory 41 stores therein a model 100 described below, for example. The storage area of the memory 41 may be located within the X-ray CT apparatus 1 or be within an external storage apparatus connected with a network. The memory 41 is an example of a storage unit.

The display 42 displays various types of information. The display 42 displays medical images (CT images) generated by the processing circuitry 44 and a graphical user interface (GUI) for receiving various kinds of operations from an operator, for example. The information displayed on the display 42 includes images based on various kinds of medical image data such as a mask image and a CT image with the mask image superimposed thereon according to the embodiment. As the display 42, any various displays can be used as appropriate. As the display 42, a liquid crystal display (LCD), a cathode ray tube (CRT) display, an organic electro luminescence display (OELD), or a plasma display can be used, for example.

The display 42 may be provided anywhere in the control room. The display 42 may be provided in the frame 10. The display 42 may be of a desktop type or include a tablet terminal or the like that can wirelessly communicate with the console 40 main body. One or two or more projectors may be used as the display 42. The display 42 is an example of a display unit.

The input interface 43 receives various kinds of input operations from the operator, converts the received input operations into electric signals, and outputs them to the processing circuitry 44. The input interface 43 receives collection conditions when collecting the projection data, reconstruction conditions when reconstructing the CT image, and image processing conditions when generating a post-processed image from the CT image from the operator, for example. The input interface 43 receives operations related to the setting of a region of interest in a diffusion-weighted image (DWI) from the operator, for example.

As the input interface 43, a mouse, a keyboard, a trackball, a switch, a button, a joystick, a touchpad, or a touch panel display can be used as appropriate, for example. In the present embodiment, the input interface 43 is not limited to those including these physical operating components. Examples of the input interface 43 include electric signal processing circuitry receiving an electric signal corresponding to an input operation from an external input device provided separately from the apparatus and outputting this electric signal to the processing circuitry 44. The input interface 43 may be provided in the frame 10. The input interface 43 may include a tablet terminal or the like that can wirelessly communicate with the console 40 main body. The input interface 43 is an example of an input unit.

The processing circuitry 44 controls the operation of the entire X-ray CT apparatus 1. The processing circuitry 44 has a processor and memories such as a ROM and a RAM as hardware resources. The processing circuitry 44 executes a system control function 441, an image generation function 442, an image processing function 443, a learning data generation function 444, a learning function 445, an inference function 446, a display control function 447 and the like by the processor executing a computer program loaded onto the memory. The processing circuitry 44 is an example of a processing unit.

In the system control function 441, the processing circuitry 44 controls various kinds of functions of the processing circuitry 44 based on input operations received from the operator via the input interface 43. The processing circuitry 44 controls CT scan performed by the frame 10, for example. The processing circuitry 44 acquires the detection data obtained by the CT scan. The processing circuitry 44 may acquire the detection data about the subject P from the outside of the X-ray CT apparatus 1.

In the image generation function 442, the processing circuitry 44 generates data in which pre-processing such as logarithmic conversion processing, offset correction processing, inter-channel sensitivity correction processing, or beam hardening correction is performed on the detection data output from the DAS 18. The processing circuitry 44 stores the generated data in the memory 41. The data before the pre-processing (the detection data) and the data after the pre-processing may collectively be referred to as the projection data. The processing circuitry 44 performs reconstruction processing using the filtered back projection method, the successive approximation reconstruction method, machine learning, or the like on the generated projection data (the projection data after the pre-processing) to generate CT image data. The processing circuitry 44 stores the generated CT image data in the memory 41.

Thus, the system control function 441 and the image generation function 442 acquire the projection data about the subject P. The processing circuitry 44 implementing the system control function 441 and the image generation function 442 is an example of an acquisition unit.

In the image processing function 443, the processing circuitry 44 converts the CT image data generated by the image generation function 442 into tomographic image data of a given section or three-dimensional image data by a known method based on input operations received from the operator via the input interface 43. The processing circuitry 44 applies three-dimensional image processing such as volume rendering, surface rendering, image value projection processing, multi-planar reconstruction (MPR) processing, or curved MPR (CPR) processing to the CT image data to generate rendered image data in a given viewpoint direction, for example. The generation of the three-dimensional image data, that is, volume data such as the rendered image data in a given viewpoint direction may be performed directly by the image generation function 442. The processing circuitry 44 stores the tomographic image data or the three-dimensional image data in the memory 41.

In the learning data generation function 444, the processing circuitry 44 performs generation processing to generate data for learning the model 100. The generation processing for the data for learning the model 100 will be described below. The processing circuitry 44 implementing the learning data generation function 444 is an example of a learning data generation unit.

In the learning function 445, the processing circuitry 44 performs learning processing to train the model 100 using a data set for learning generated by the learning data generation function 444. The learning processing for the model 100 will be described below. The processing circuitry 44 implementing the learning function 445 is an example of a learning unit.

In the inference function 446, the processing circuitry 44 performs identification processing to identify a region of interest in the projection data based on the learned model 100 and the projection data. The identification processing for the region of interest will be described below. The processing circuitry 44 implementing the inference function 446 is an example of an identification unit.

In the display control function 447, the processing circuitry 44 displays images on the display 42 based on the various kinds of image data generated by the image processing function 443. The images to be displayed on the display 42 include a reconstructed image as a display image with the identified region of interest highlighted on the image. The display may be performed by displaying a mask image indicating the region of interest superimposed on the reconstructed image or be performed based on reconstructed image data for display with mask image data synthesized. The images to be displayed on the display 42 include a CT image based on the CT image data, a sectional image based on the sectional image data of a given section, and a rendered image in a given viewpoint direction based on the rendered image data in a given viewpoint direction. The images to be displayed on the display 42 include an image for displaying an operation screen and an image for displaying notifications and warnings to the operator. The processing circuitry 44 implementing the display control function 447 is an example of a display controller.

The image data showing the display image with the identified region of interest highlighted on the image may be generated by either function of the image processing function 443 and the display control function 447.

Each of the functions 441 to 447 is not limited to being implemented by a single piece of processing circuitry. Each of the functions 441 to 447 may be implemented by combining a plurality of independent processors with each other to form the processing circuitry 44 and causing each of the processors to execute each computer program. Each of the functions 441 to 447 may be implemented distributed or integrated as appropriate in a single piece or a plurality of pieces of processing circuitry.

Although the console 40 has been described as a single console executing a plurality of functions, separate consoles may execute the functions. The functions of processing circuitry 44 such as the image generation function 442, the image processing function 443, the learning data generation function 444, the learning function 445, and the inference function 446 may be distributed, for example.

Part or the whole of the processing circuitry 44 is not limited to being included in the console 40 and may be included in an integrated server collectively performing processing on the detection data acquired by a plurality of medical image diagnostic apparatuses.

At least one piece of processing out of post-processing, generation processing, learning processing, identification processing, and display processes may be performed by either the console 40 or an external workstation. The processing may be processed by both the console 40 and the workstation at the same time. As the workstation, a computer having a processor implementing functions corresponding to the respective pieces of processing and memories such as a ROM and a RAM as hardware resources can be used as appropriate, for example.

In the reconstruction of the X-ray CT image data, either reconstruction system of a full-scan reconstruction system and a half-scan reconstruction system may be applied. In the image generation function 442, the processing circuitry 44 uses the projection data for the surroundings of the subject P, or 360 degrees in the full-scan reconstruction system, for example. In the half-scan reconstruction system, the processing circuitry 44 uses the projection data for 180 degrees+a fan angle. In the following, for the sake of the simplicity of description, it is assumed that the processing circuitry 44 uses the full-scan reconstruction system performing reconstruction using the projection data for the surroundings of the subject P, or 360 degrees.

The technology according to the present embodiment can also be applied to both single-tube X-ray computed tomography apparatuses and what is called multi-tube X-ray computed tomography apparatuses in which a plurality of pairs of an X-ray tube and a detector are installed in a rotating ring.

The technology according to the present embodiment can also be applied to the X-ray CT apparatus 1 configured to enable imaging by a dual-energy system. In this case, the X-ray high voltage apparatus 14 can alternately switch the energy spectrum of the X-rays emitted from the X-ray tube 11 by fast switching between two kinds of voltage values, for example. That is to say, the X-ray CT apparatus 1 is configured to be capable of collecting the projection data in each collection view while modulating a tube voltage at timing following a control signal for tube voltage modulation. By imaging a subject at different tube voltages, light and shade contrast in the CT image can be improved based on the energy permeability of a material for each X-ray energy spectrum.

It is assumed that the X-ray CT apparatus 1 according to the present embodiment is configured to read an electric signal from the X-ray detector 12 by a sequential reading system.

The X-ray CT apparatus 1 according to the present embodiment may be configured as an upright CT. In this case, a patient support mechanism configured to be capable of supporting the subject P in an upright position and moving it along a rotating shaft of the rotating part of the frame 10 may be provided in place of the movement of the couchtop 33. The X-ray CT apparatus 1 according to the present embodiment may be configured as a mobile CT in which the frame 10 and the couch 30 are movable.

Figure 2:
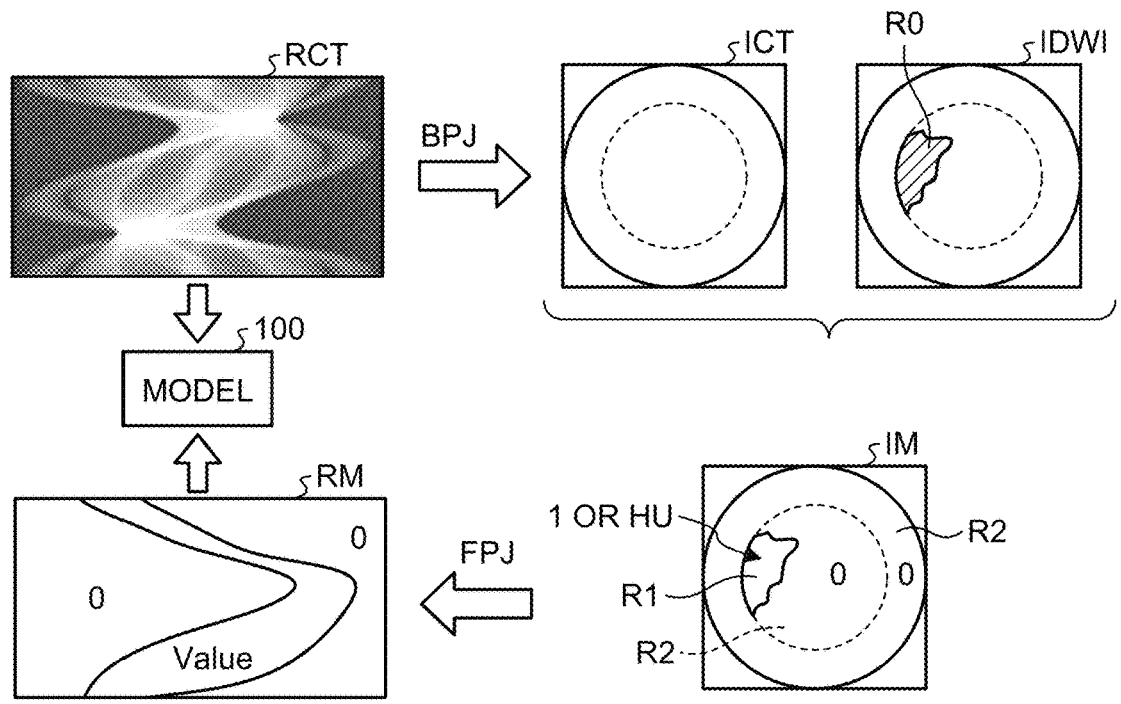
FIG. 2 is a diagram for illustrating the raw data-based learning of a model according to the embodiment.

The following describes the generation processing for the data for learning the model 100 and the learning processing for the model 100 according to the present embodiment in more detail with reference to the drawings. FIG. 2 is a diagram for illustrating the raw data-based learning of the model 100 according to the embodiment.

The processing circuitry 44 acquires projection data RCT obtained by the X-ray CT apparatus 1 and the data of a CT image ICT obtained by image reconstruction based on the projection data RCT from the memory 41, for example. The processing circuitry 44 acquires the data of a diffusion-weighted image IDWI obtained by an MRI apparatus from the memory 41, for example. The processing circuitry 44 may acquire the data of the diffusion-weighted image IDWI from the MRI apparatus or PACS via a network such as a hospital network. It is assumed that the projection data RCT and the data of the diffusion-weighted image IDWI are data about the same part of the same subject. The projection data RCT is an example of the second medical image data. The data of the diffusion-weighted image IDWI is an example of the third medical image data. The diffusion-weighted image IDWI is an image much higher in the ability to detect hyperacute cerebral infarction than the CT image ICT.

The processing circuitry 44 identifies a region R0 of ischemia in the diffusion-weighted image IDWI from the diffusion-weighted image IDWI based on an input result by the operator received by the input interface 43, for example. The processing circuitry 44 aligns the diffusion-weighted image IDWI and the CT image ICT with each other. The processing circuitry 44 generates a mask image IM by extracting a region R1 corresponding to the region R0 of ischemia on the image of the CT image ICT. The region R1 is an example of the region of interest.

The processing circuitry 44, in the mask image IM, retains a CT value of the CT image ICT for the region R1. On the other hand, the processing circuitry 44, in the mask image IM, discards the CT value of the CT image ICT for another region R2 than the region R1 in the region on the image of the CT image ICT. Consequently, in the mask image IM, the CT value is present only in the extracted region R1.

The processing circuitry 44, in the mask image IM, for the region R1, may normalize the CT value of the CT image ICT or give it a value of "1". In both cases, for the region R2, the CT value of the CT image ICT is discarded and is given a value of "0".

The processing circuitry 44 generates a sinogram RM by forward projection based on the mask image IM taking into account the geometry of the X-ray CT apparatus 1 and the physical characteristics of the X-rays. As illustrated in FIG. 2, in the sinogram RM, there is a value in the region of interest corresponding to the region R1.

The processing circuitry 44 performs the learning processing to train the model 100 using the projection data RCT and the generated sinogram RM. Specifically, parameters of the model 100 are determined so as to output a sinogram with a value in the region R1 of ischemia, that is, the region of interest in response to the input of the projection data. That is to say, the learned model 100 is a parameterized composite function with a plurality of functions composed outputting, with the projection data as input, the sinogram indicating the region of interest in the projection data.

The parameterized composite function is defined by a combination of a plurality of adjustable functions and parameters. This model 100 may be any parameterized composite function satisfying the above requirements; it is assumed to be a multilayer network model. The model 100 is a deep neural network (DNN), as an example. This DNN may be a DNN of any structure; Residual Network (ResNet), Dense Convolutional Network (DenseNet), or U-Net can be used, for example. The configuration and the initial values of the parameters of the model 100 may be set in advance and be stored in the memory 41, for example.

The model 100 can be prepared for each lesion, each type of the medical image diagnostic apparatus, and each part of the subject, for example.

Figure 3:
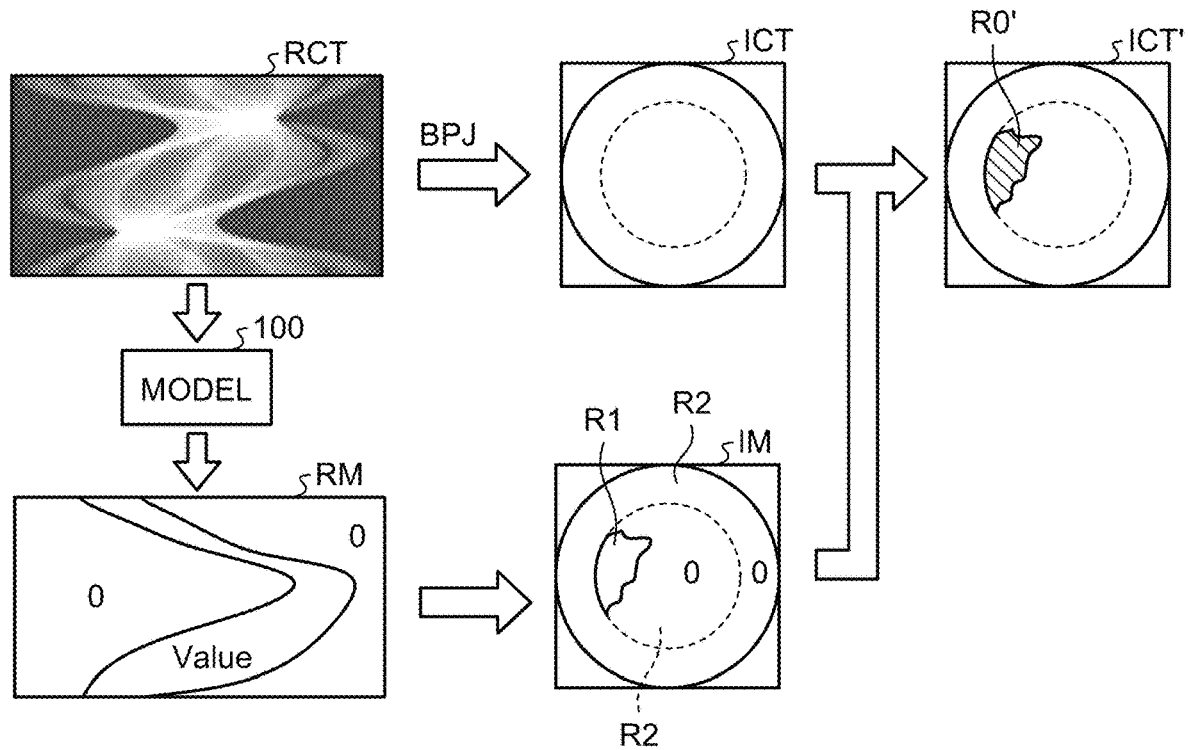
FIG. 3 is a diagram for illustrating raw data-based inference by the model according to the embodiment.

The following describes the identification processing for the region of interest according to the embodiment in more detail with reference to the drawings. FIG. 3 is a diagram illustrating raw data-based inference by the model 100 according to the embodiment.

The processing circuitry 44 acquires the projection data RCT obtained by the X-ray CT apparatus 1 and the data of the CT image ICT obtained by the image reconstruction based on the projection data RCT from the memory 41, for example. The projection data RCT is an example of the first medical image data.

The processing circuitry 44 inputs the projection data RCT to the learned model 100. The processing circuitry 44 acquires the sinogram RM from the learned model 100 corresponding to the input of the projection data RCT. The processing circuitry 44 generates the mask image IM by image reconstruction based on the acquired sinogram RM.

The processing circuitry 44 superimposes the mask image IM on the CT image ICT to display a CT image ICT', in which a region R0' of ischemia is highlighted, on the display 42. The processing circuitry 44 changes the color of the region R0' of ischemia from that of the other region in the CT image ICT' to display the region R0' of ischemia in a highlighted manner.

Figure 4:
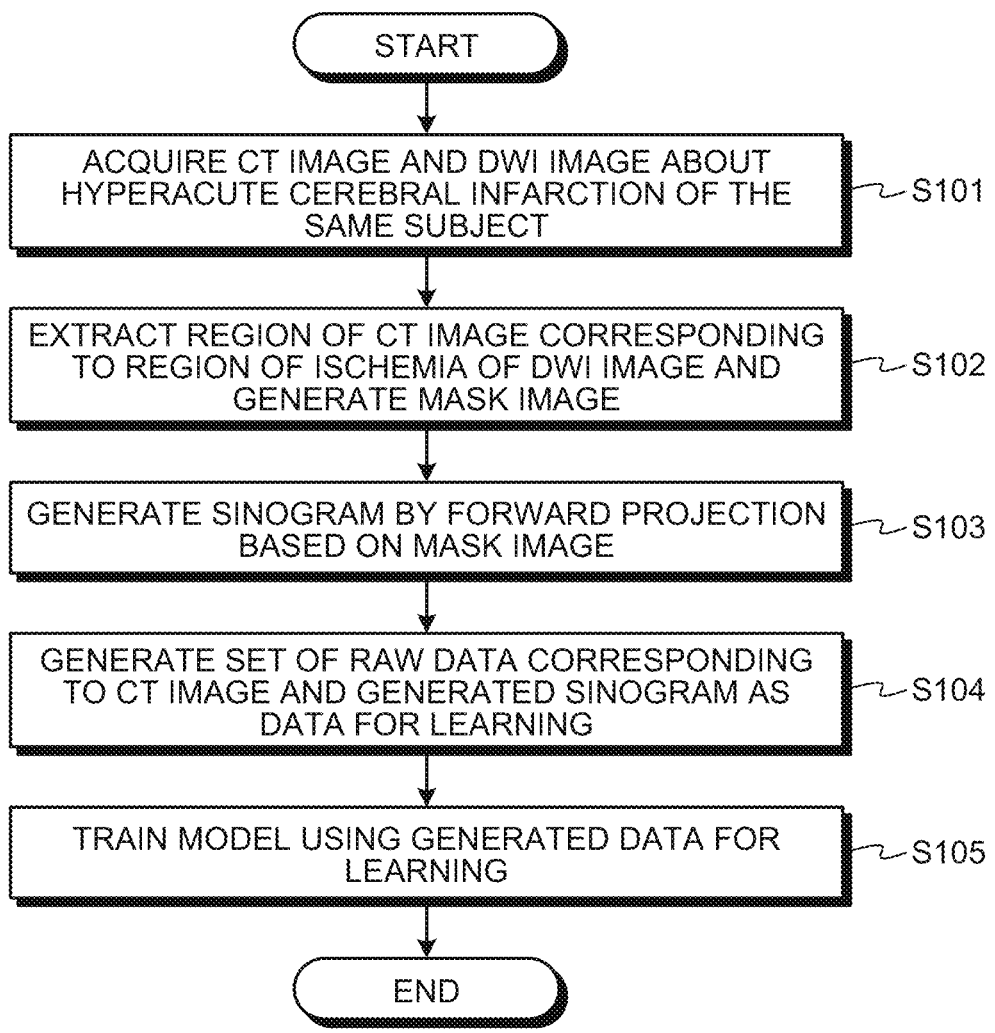
FIG. 4 is a flowchart of an example of raw data-based learning processing according to the embodiment.

FIG. 4 is a flowchart of an example of raw data-based learning processing according to the embodiment.

First, the learning data generation function 444 acquires CT image data and DWI image data about hyperacute cerebral infarction of the same subject (S101).

The learning data generation function 444 generates a mask image (S102). Specifically, the learning data generation function 444 identifies a region of ischemia in a DWI image based on an input result by the operator received by the input interface 43, for example. The learning data generation function 444 extracts a region of the CT image corresponding to the identified region of ischemia. The learning data generation function 444 generates a mask image by deleting a CT value corresponding to the other region than the extracted region of the CT image data. The deletion of the CT value means padding it with a value of "0". The learning data generation function 444 may normalize the CT value of the extracted region of the CT image data or pad the CT value of the extracted region of the CT image data with a value of "1".

The learning data generation function 444 generates a sinogram by forward projection based on the mask image (S103). This sinogram can also be represented as infarction weight, which indicates the region of ischemia, that is, the distribution of infarct.

The learning data generation function 444 generates a set of the projection data (raw data) corresponding to the CT image and the generated sinogram as data for learning (S104).

Then the learning function 445 performs learning processing to train the model 100 using the generated data set for learning (S105).

Figure 5:
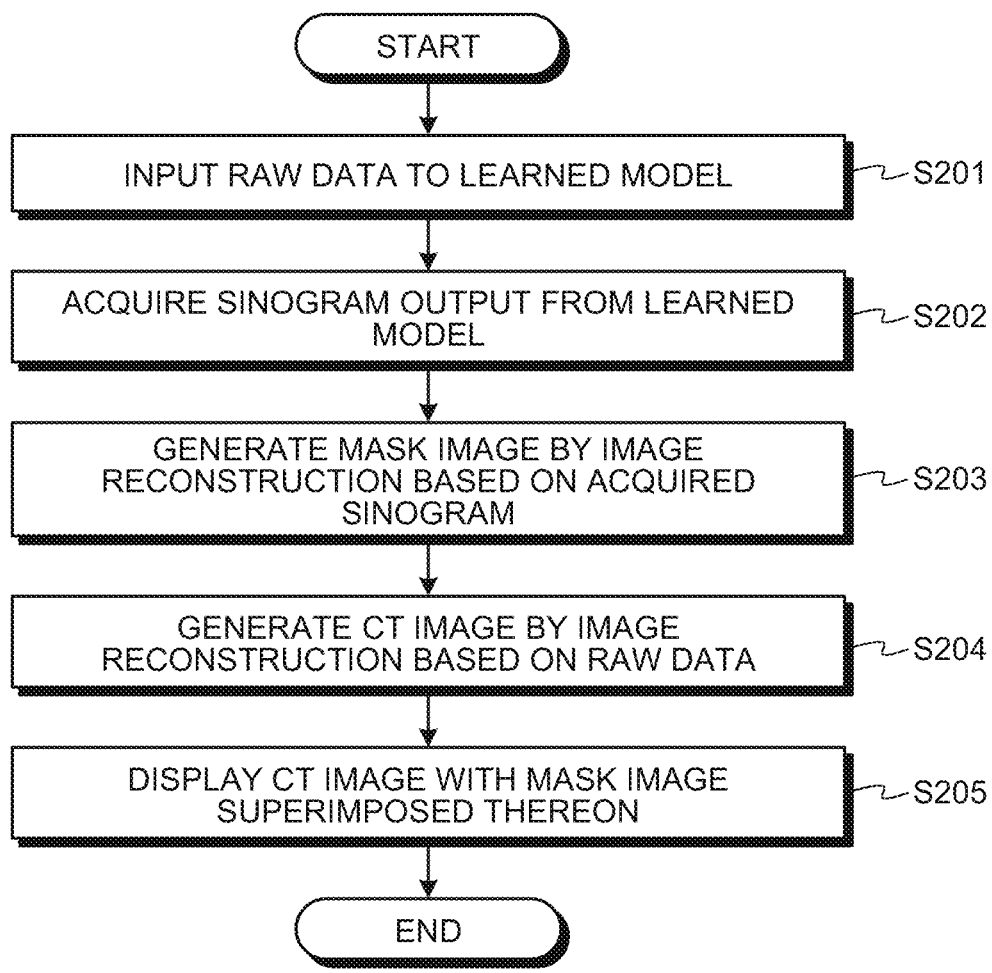
FIG. 5 is a flowchart of an example of raw data-based inference processing according to the embodiment.

FIG. 5 is a flowchart of an example of raw data-based inference processing according to the embodiment.

The inference function 446 inputs the projection data (raw data) to the learned model 100 (S201). The inference function 446 acquires a sinogram output from the learned model 100 in response to the input of the projection data (S202).

The image generation function 442 generates mask image data by image reconstruction based on the acquired sinogram (S203). In addition, the image generation function 442 generates CT image data by image reconstruction based on the projection data (S204). The display control function 447 displays a CT image with a mask image superimposed thereon on the display 42 (S205).

Thus, in the X-ray CT apparatus 1 in which the medical image processing apparatus according to the embodiment is installed, the processing circuitry 44 is configured to be capable of implementing the system control function 441, the image generation function 442, the learning function 445, and the inference function 446. In the system control function 441 and the image generation function 442, the processing circuitry 44 acquires the projection data of the subject P. The learning function 445 trains the model 100 based on the projection data and the diffusion-weighted image data about the same subject. The inference function 446 identifies the region of interest in the projection data based on the learned model 100 and the projection data of the subject P.

With this configuration, the X-ray CT apparatus 1 can detect hyperacute cerebral infarction with accuracy comparable to that of MRI images, which have higher imaging sensitivity than that of CT images, while maintaining the rapidity of CT image reconstruction. In other words, the technology according to the embodiment can improve the diagnostic ability of medical image diagnosis.

In the X-ray CT apparatus 1 in which the medical image processing apparatus according to the embodiment is installed, the processing circuitry 44 is configured to be capable of further implementing the display control function 447. The display control function 447 displays the CT image with the mask image superimposed thereon on the display 42. With this configuration, the X-ray CT apparatus 1 can display the CT image in which the region of ischemia is highlighted by changing its color, for example. In other words, the technology according to the embodiment can improve the diagnostic ability of medical image diagnosis.

Second Embodiment

The present embodiment mainly describes differences from the first embodiment.

Figure 6:
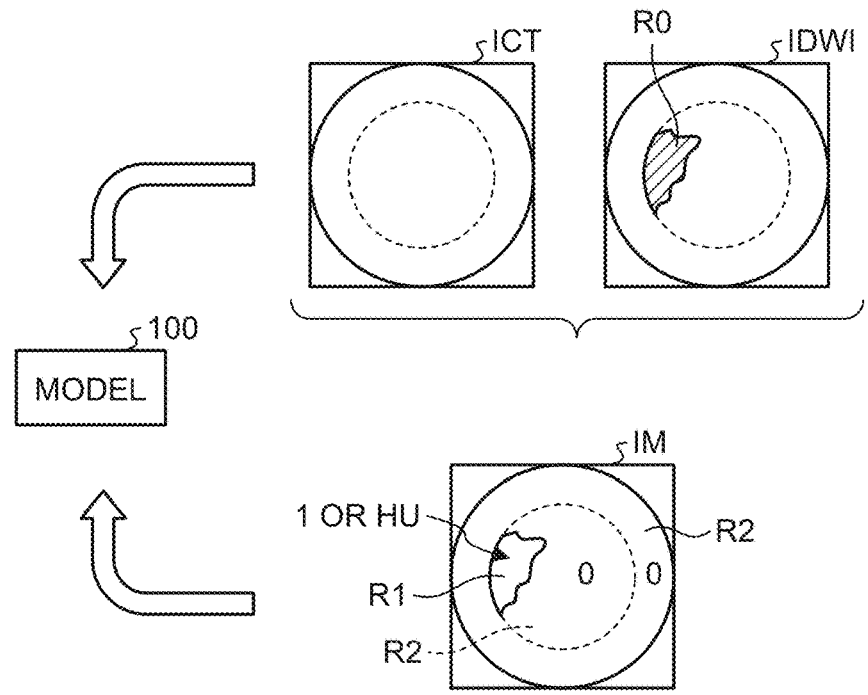
FIG. 6 is a diagram for illustrating the image-based learning of the model according to the embodiment.

FIG. 6 is a diagram for illustrating the image-based learning of the model 100 according to the embodiment.

The processing circuitry 44 acquires the data of the CT image ICT obtained by the X-ray CT apparatus 1 from the memory 41, for example. The processing circuitry 44 acquires the data of the diffusion-weighted image IDWI obtained by the MRI apparatus from the memory 41, for example. It is assumed that the data of CT image ICT and the data of diffusion-weighted image IDWI are data about the same part of the same subject. The data of the CT image ICT data is an example of the second medical image data. The data of the diffusion-weighted image IDWI is an example of the third medical image data.

The processing circuitry 44 generates the data of the mask image IM by extracting the region R1 on the image of the CT image ICT corresponding to the region R0 of ischemia in the diffusion-weighted image IDWI.

The processing circuitry 44 performs learning processing to train the model 100 using the data of the CT image ICT and the generated data of the mask image IM. Specifically, parameters of the model 100 are determined so as to output a mask image with a value in the region R1 of ischemia, that is, the region of interest in response to the input of the CT image data.

Figure 7:
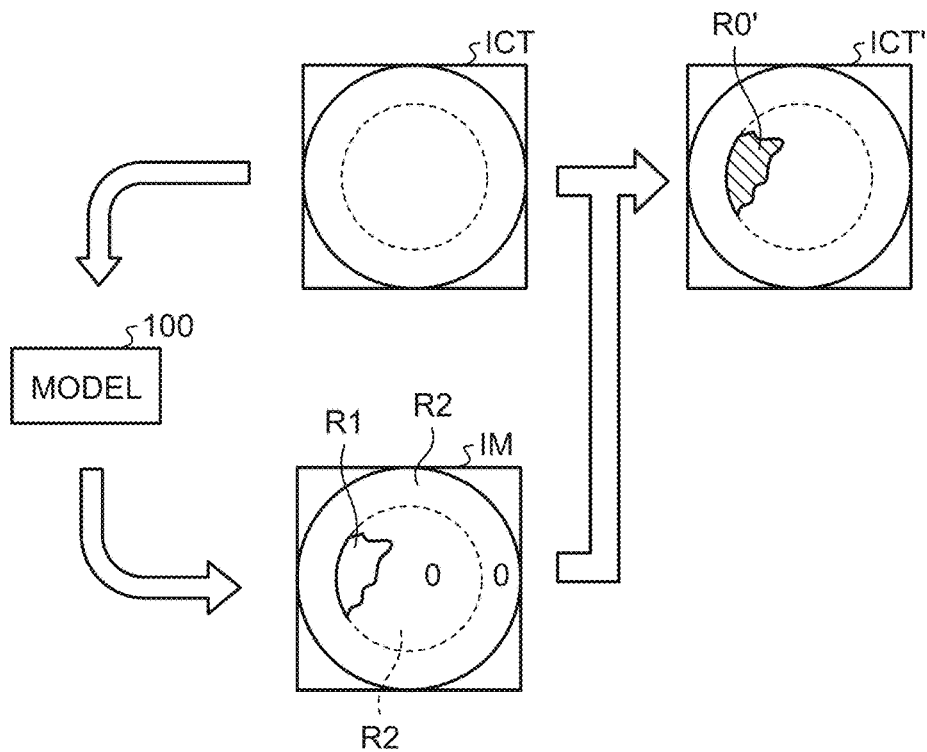
FIG. 7 is a diagram for illustrating image-based inference by the model according to the embodiment.

FIG. 7 is a diagram for illustrating image-based inference by the model 100 according to the embodiment.

The processing circuitry 44 acquires the data of the CT image ICT obtained by the X-ray CT apparatus 1 from the memory 41, for example. The data of the CT image ICT is an example of the first medical image data.

The processing circuitry 44 inputs the data of the CT image ICT to the learned model 100. The processing circuitry 44 acquires the data of the mask image IM from the learned model 100 corresponding to the input of the data of the CT image ICT.

The processing circuitry 44 superimposes the mask image IM on the CT image ICT to display the CT image ICT', in which the region R0' of ischemia is highlighted, on the display 42.

Figure 8:
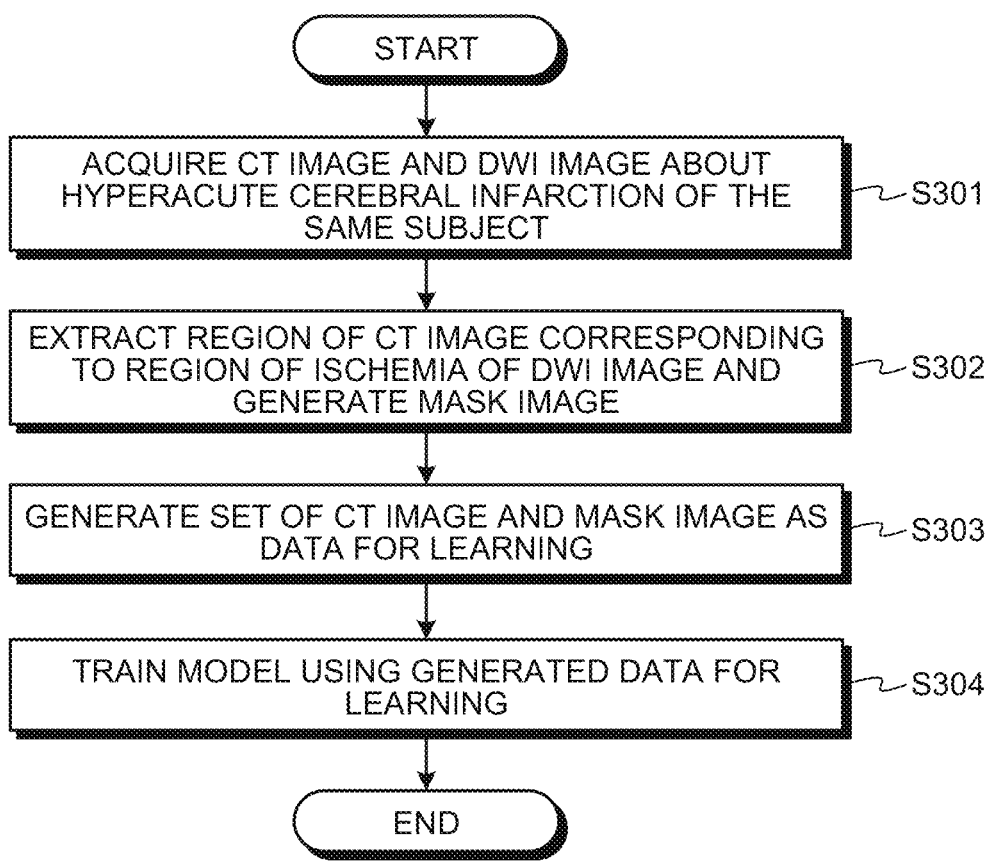
FIG. 8 is a flowchart of an example of image-based learning processing according to an embodiment.

FIG. 8 is a flowchart of an example of image-based learning processing according to the embodiment.

The learning data generation function 444 acquires CT image data and DWI image data about hyperacute cerebral infarction of the same subject in the same manner as S101 in FIG. 4 (S301). The learning data generation function 444 generates a mask image in the same manner as S102 in FIG. 4 (S302).

The learning data generation function 444 generates a set of CT image data and mask image data as data for learning (S303). Then the learning function 445 performs learning processing to train the model 100 using the generated data set for learning (S304).

Figure 9:
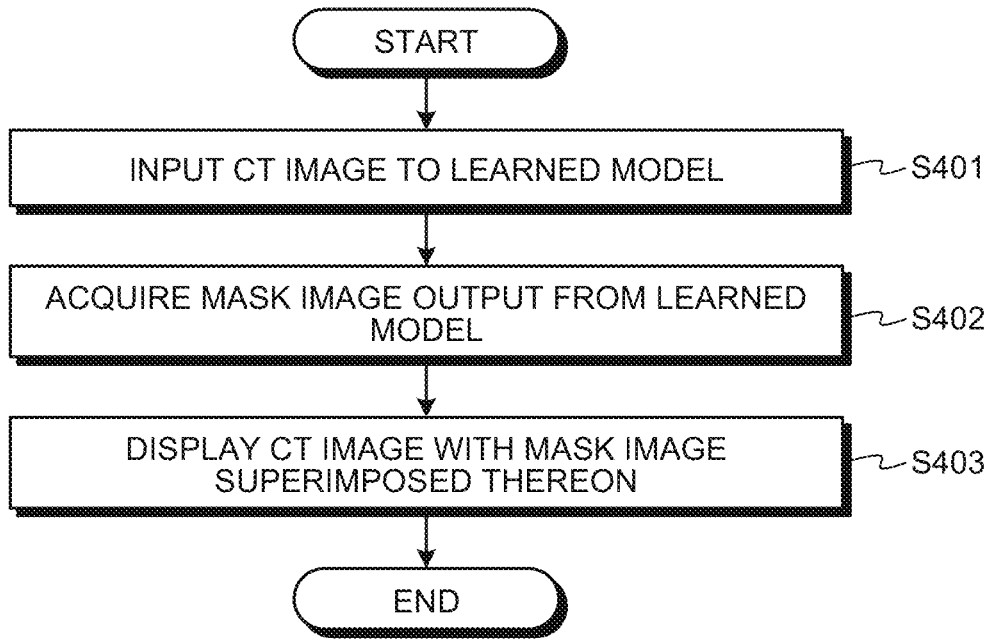
FIG. 9 is a flowchart of an example of image-based inference processing according to the embodiment.

FIG. 9 is a flowchart of an example of image-based inference processing according to the embodiment.

The inference function 446 inputs CT image data to the learned model 100 (S401). The inference function 446 acquires mask image data output from the learned model 100 in response to the input of the CT image data (S402). The display control function 447 displays a CT image with a mask image superimposed thereon on the display 42 in the same manner as S205 in FIG. 5 (S403).

Thus, in the X-ray CT apparatus 1 in which the medical image processing apparatus according to the embodiment is installed, the learning processing and the inference processing, for example, are performed on an image basis, whereas in the first embodiment they are performed on a raw data basis. With this configuration as well, the same effect as that of the first embodiment can be obtained.

Third Embodiment

Figure 10:
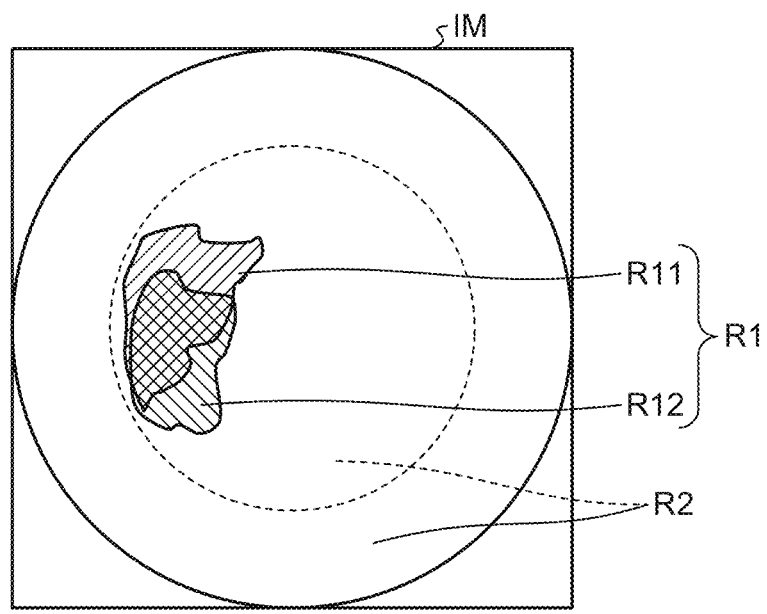
FIG. 10 is a diagram for illustrating a combination of raw data-based processing and image-based processing according to an embodiment.

The raw data-based processing according to the first embodiment and the image-based processing according to the second embodiment can be combined with each other. FIG. 10 is a diagram for illustrating a combination of the raw data-based processing and the image-based processing according to an embodiment.

It is assumed that a region R11 of ischemia has been estimated as illustrated in FIG. 10 based on the raw data-based inference processing according to the first embodiment. On the other hand, it is assumed that a region R12 of ischemia has been estimated as illustrated in FIG. 10 based on the image-based inference processing according to the second embodiment.

For hyperacute cerebral infarction, for example, detection in an early stage and performing appropriate treatment are required, and it is desirable to reduce the occurrence of false negatives such as missing of an early CT sign (an early ischemic sign).

Given this, in the X-ray CT apparatus 1 in which the medical image processing apparatus according to the present embodiment is installed, the region R1 of ischemia is identified as the logical sum of the region R11 of ischemia estimated based on the raw data-based inference processing and the region R12 of ischemia estimated based on the image-based inference processing. In other words, the mask image IM according to the present embodiment includes the region R1 identified so as to include at least either the regions R11 of ischemia estimated based on the raw data-based inference processing or the region R12 of ischemia estimated based on the image-based inference processing.

With this configuration, an effect of making it possible to further inhibit the occurrence of false negatives compared with the embodiments described above can be obtained.

Although the embodiments describe a case in which the learning processing and the inference processing are performed based on the DWI image data obtained by the MRI apparatus while exemplifying cerebral infarction, this is not limiting. In place of the DWI image data, image data obtained by various kinds of medical image diagnostic apparatuses can be used as appropriate, for example. The image data used in place of the DWI image data may be any image data that can be mapped with a CT image. As an example, in place of the DWI image data, image data obtained by a medical image diagnostic apparatus such as a PET apparatus, a SPECT apparatus, an X-ray apparatus, an angiograph apparatus, an ultrasonic diagnostic apparatus, or a thermograph apparatus can be used, for example.

The learning processing and the inference processing according to the embodiments described above may be performed based on image data differing from each other in the type of at least one of a scan condition during imaging, an applied reconstruction condition, and applied image processing, not limited to the medical image diagnostic apparatus used for imaging. In other words, in place of the DWI image data, the CT image data differing from each other in the type of at least one of the scan condition during imaging, the applied reconstruction condition, and the applied image processing can be used.

The projection data RCT as an example of the second medical image data is preferably the same type image data as the projection data RCT as an example of the first medical image data. However, the projection data RCT as an example of the first medical image data and the projection data RCT as an example of the second medical image data may be image data differing from each other in the type of at least one of the scan condition during imaging, the applied reconstruction condition, and the applied image processing, for example. Similarly, the data of the CT image ICT as an example of the second medical image data is preferably the same type of image data as the data of the CT image ICT as an example of the first medical image data. However, the data of the CT image ICT as an example of the first medical image data and the data of the CT image ICT as an example of the second medical image data may be image data differing from each other in the type of at least one of the scan condition during imaging, the applied reconstruction condition, and the applied image processing, for example.

The term "processor" used in the above description means a circuit such as a CPU, a graphics processing unit (GPU), an ASIC, or a programmable logic device (PLD), for example. PLDs include simple programmable logic devices (SPLDs), complex programmable logic devices (CPLDs), and field programmable gate arrays (FPGAs). The processor implements its functions by reading and executing a computer program stored in a memory circuit. The storage circuit in which the computer program is stored is a computer-readable, non-transitory storage medium. In place of storing the computer program in the memory circuit, the computer program may directly be incorporated into the circuit of the processor. In this case, the processor implements its functions by reading and executing the computer program incorporated into the circuit. Not executing the computer program, the function corresponding to the computer program may be implemented by a combination of logic circuits. Each processor of the present embodiment is not limited to being configured as a single circuit for each processor and may be configured as one processor by combining a plurality of independent circuits to implement its functions. Furthermore, the components in FIG. 1 may be integrated into a single processor to implement their functions.

At least one of the embodiments described above can improve the diagnostic ability of medical image diagnosis.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising processing circuitry configured to
acquire first medical image data and
identify a region of interest in the first medical image data based on a learned model and the first medical image data, wherein
the learned model is trained based on
second medical image data corresponding to the first medical image data and
third medical image data different from the first medical image data in type and related to the same subject as a subject of the second medical image data, and
at least part of the third medical image data is higher in imaging sensitivity for a region of the subject corresponding to the region of interest than the second medical image data.

2. The medical image processing apparatus according to claim 1, wherein the first medical image data and the second medical image data are data obtained by the same type of medical image diagnostic apparatus.

3. The medical image processing apparatus according to claim 1, wherein the second medical image data and the third medical image data differ from each other in at least one of a medical image diagnostic apparatus used for imaging, a scan condition during imaging, an applied reconstruction condition, and applied image processing.

4. The medical image processing apparatus according to claim 2, wherein the second medical image data and the third medical image data differ from each other in at least one of a medical image diagnostic apparatus used for imaging, a scan condition during imaging, an applied reconstruction condition, and applied image processing.

5. The medical image processing apparatus according to claim 1, wherein the first medical image data is projection data or reconstructed image data generated by image reconstruction based on the projection data.

6. The medical image processing apparatus according to claim 1, wherein
the first medical image data is reconstructed image data, and
the processing circuitry is configured to generate a display image in which the region of interest identified on an image of a reconstructed image indicated by the reconstructed image data is highlighted.

7. The medical image processing apparatus according to claim 1, wherein
the first medical image data is projection data, and
the processing circuitry is configured to generate a display image in which the region of interest identified on an image of a reconstructed image obtained by image reconstruction based on the projection data is highlighted.

8. The medical image processing apparatus according to claim 1, wherein
the first medical image data is projection data and reconstructed image data generated by image reconstruction based on the projection data, and
the processing circuitry is configured to
identify a first region of interest in the projection data based on the learned model and the projection data,
identify a second region of interest in the reconstructed image data based on the learned model and the reconstructed image data, and
identify a logical sum of the first region of interest and the second region of interest as the region of interest.

9. The medical image processing apparatus according to claim 1, wherein
the second medical image data and the third medical image data are each projection data or reconstructed image data generated by image reconstruction based on the projection data, and
the processing circuitry is configured to
identify a region of interest on an image of a reconstructed image corresponding to the third medical image data,
generate a mask image in which a CT value of another region than a region corresponding to the region of interest identified on the image of the reconstructed image in the second medical image data is deleted, and
generate data for learning the model using mask image data indicating the mask image.

10. An X-ray computed tomography (CT) apparatus comprising:
an X-ray tube generating X-rays;
an X-ray detector detecting X-rays from the X-ray tube having passed through a subject; and
processing circuitry configured to, based on a learned model and first medical image data, which is projection data based on output of the X-ray detector or reconstructed image data image-reconstructed based on the projection data, identify a region of interest in the first medical image data, wherein
the learned model is trained based on second medical image data corresponding to the first medical image data and third medical image data different from the first medical image data in type and related to the same subject as a subject of the second medical image data, and
at least part of the third medical image data is higher in imaging sensitivity for a region of the subject corresponding to the region of interest than the second medical image data.

11. A method of medical image processing comprising:
acquiring first medical image data; and
identifying a region of interest in the first medical image data based on a learned model and the first medical image data, wherein
the learned model is trained based on second medical image data corresponding to the first medical image data and third medical image data different from the first medical image data in type and related to the same subject as a subject of the second medical image data, and
at least part of the third medical image data is higher in imaging sensitivity for a region of the subject corresponding to the region of interest than the second medical image data.

12. A computer program product storing a program executed by a computer, the program causing the computer to execute:
  acquiring first medical image data; and
  identifying a region of interest in the first medical image data based on a learned model and the first medical image data, wherein
  the learned model is trained based on second medical image data corresponding to the first medical image data and third medical image data different from the first medical image data in type and related to the same subject as a subject of the second medical image data, and
  at least part of the third medical image data is higher in imaging sensitivity for a region of the subject corresponding to the region of interest than the second medical image data.

* * * * *